United States Patent
Yu et al.

(10) Patent No.: US 6,548,687 B1
(45) Date of Patent: Apr. 15, 2003

(54) CHROMIUM L-THREONATE, PROCESS FOR PREPARATION OF THE SAME AND THEIR USE

(76) Inventors: Kai Yu, 31-6-401 Dong Wang Zhuang, Haidain District, Beijing, 100083 (CN); Fuping Kou, 31-6-501 Dong Wang Zhuang, Haidian District, Beijing, 100083 (CN); Zhiwen Wang, 31-6-602 Dong Wang Zhuang, Haidian District, Beijing, 10083 (CN)

( * ) Notice: Subject to any disclaimer, the term of this patent is extended or adjusted under 35 U.S.C. 154(b) by 0 days.

(21) Appl. No.: 09/763,176

(22) PCT Filed: Aug. 18, 1999

(86) PCT No.: PCT/CN99/00120

§ 371 (c)(1), (2), (4) Date: Feb. 20, 2001

(87) PCT Pub. No.: WO00/10962

PCT Pub. Date: Mar. 2, 2000

(30) Foreign Application Priority Data

Aug. 18, 1998 (CN) .......................... 98117192 A

(51) Int. Cl.$^7$ .......................... C07F 11/00; A61K 31/28
(52) U.S. Cl. .......................... 556/61; 514/492
(58) Field of Search .......................... 556/61; 514/492

(56) References Cited

U.S. PATENT DOCUMENTS 4,822,816 A  4/1989  Markham .................... 514/474

FOREIGN PATENT DOCUMENTS

| CN | 1143464 A | 2/1997 |
| CN | 1194865 A | 10/1998 |
| CN | 1200366 A | 12/1998 |

OTHER PUBLICATIONS

Chemical Journal of Chinese Universities vol. 19, No. 6, p. 849–853, 1998.

Beverly A, et al. "Metabolic Profiles of Urinary Organic Acids Recovered from Absorbent Filter Paper" Clin Chem, 33/4, 572–576, 1987.

F.Dubois, et al. "Role Physiologique et Interet en Pathologie Humaine" Path Biol, 1991, 39(8), 801–808.

Anthony J.V, et al. "Comparison of the Anti–Scorbutic Activity of L–Ascorbic Acid and Ester C in the Non–Ascorbate Synthesizing Osteogenic Disorder Shionogi (ODS) Rat" Life Sciences, 48, 2275–2281, 1991.

Tatsuya Yamagishi, et al. "Total Synthesis of Trehalase Inhibitor Salbostatin" Bioor. Med. Chem Let. 3(5), 487–494. 1995.

Primary Examiner—Porfirio Nazario-Gonzalez
(74) Attorney, Agent, or Firm—Rabin & Berdo, P.C.

(57) ABSTRACT

This invention involves a new kind of compound—the chromate L-threonate which molecular formula is $Cr_n(C_4H_{8-n}O_5)_3$ (n=1, 2 or 3). The chromate L-thronate can be applied to a high performance supplement of chromium(III) as well as effective hypoglycemic treatment for those diabetes patients and health care.

4 Claims, 2 Drawing Sheets

CHROMIUM L-THREONATE, PROCESS FOR PREPARATION OF THE SAME AND THEIR USE

TECHNICAL FIELD

Figure 1:
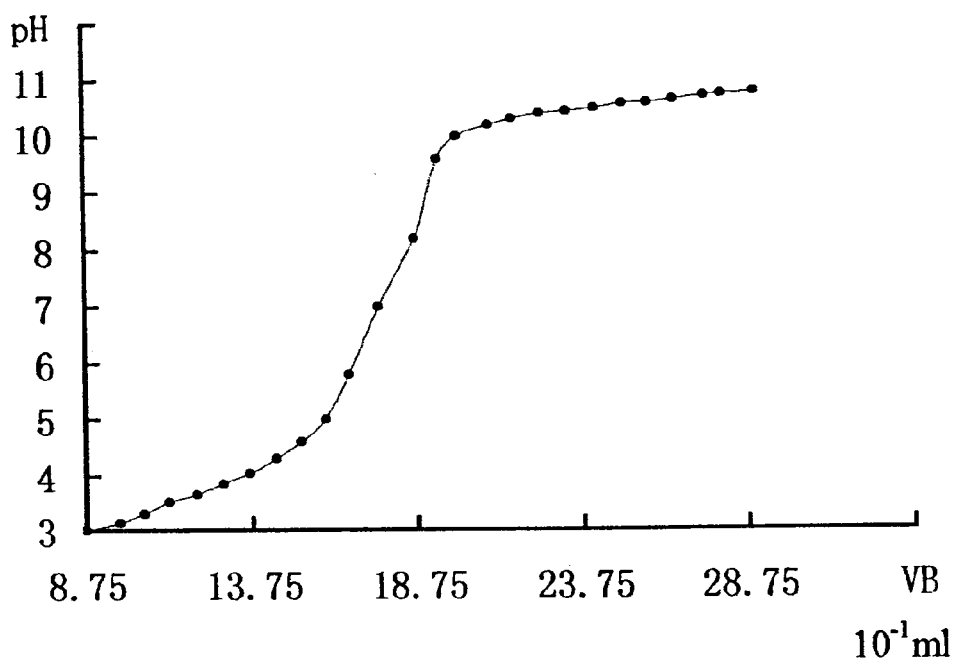

This invention involves a new kind of compound—the chromate L-threonate, as well as its synthesis and application to medicine and health care.

TECHNICAL BACKGROUND

Diabetes mellitus is one of the common diseases over the world, the morbidity is 1–2 percent among the general population. Chromium(III) is an essential trace element in human body. Scientists have confirmed there is significant relationship between the long term deficiency of chromium (III) and adult diabetes as well as arteriosclerosis. Many individuals who take much refined food are often in the above problems because of the deficiency of chromium(III) in their diet. Chromium(III) also takes on one of important components of Glucose Tolerance Factor(GTF). Organic chromium(III) is much more easily absorbable in vivo condition than the inorganic form. (F. Dubois, Pathol. Biol. 1991, 39(8), 801–808). Chromium(III) will bind with some protein (e.g. transferrin) after being absorbed, but its reaction form and structure with insulin are still indefinite.

TECHNICAL CONTENT

The purpose of this invention is to search a new kind of chromate(III) organic acid which can active and cooperate with insulin more effectively; be in definite and controllable structure; be absorbed easily in human body; supply chromium(III) effectively for humans needs; be applied to prevention and treatment of diabetes mellitus. This invention also includes the synthesis methods and application of the chromate(III).

This new kind of chromate(III) is the chromate L-threonate which molecular formula shows below:

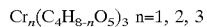

$Cr_n(C_4H_{8-n}O_5)_3$ n=1, 2, 3

L-threonic acid is one of main degradation products of Vitamin C (Clin Chem, 33, 572, 1987) and takes on positive physiological function in human body (J. Univ. PoonaSci. 2275, 1991; Technol. 54, 1–4, 1982; Bioorg. Med. Chem, 3(5), 487–494, 1995). Shourong Zhu and his colleagues reported there exists powerful affinity between metal coordination compound of L-threonate and amino acid (protein, polypeptide), that's to say, there is good compatibility between L-threonate acid and amino acid. Verlangeiri once pointed out in his research that L-threonic acid can cooperate with insulin (Life Sciences, 48, 2275, 1991). We combine L-threonic acid and Chromium(III) to produce the chromate L-threonate in this invention.

The synthesis methods of the chromate L-threonate include:
1. Take L-threonic acid as material to produce the chromate L-threonate.
2. Take calcium L-threonate as material to produce the chromate L-threonate.

According to the methods above, we can take vitamin C as raw material to synthesize calcium L-threonate, then derive the chromate L-threonate from calcium L-threonate with replacement of mild acid or cation exchange resin; also, we can take calcium L-threonate as material and derive the chromate L-threonate directly.

Chromate L-threonate, the product of this invention, can be applied to follows:
1. food additive in the form of solid or liquid for supplying the essential trace element
2. effective component in the prevention and health care of diabetes mellitus
3. combination of medicine preparation, such as tablet, capsule and other acceptable forms in pharmaceutics
4. effective ingredient of hypoglycemic medicine As a kind of combination used in the prevention and health care of diabetes mellitus, even in hypoglycemic medicine, this invention includes chromate L-threonate, calcium L-threonate, carriers and accessories of medicine.

In the combination of this invention, the chromate L-threonate takes on the primary effective component and calcium L-threonate is the secondary. According to the requirements of pharmaceutics and medicine preparation, the carriers and accessories of the combination can be any material, which is accepted by the particular medicine.

The content of chromate L-threonate and calcium L-threonate of the combination can be changed to fit different requirement of particular preparation.

The chromate L-threonate and its combination of this invention can be taken by oral administration in almost conditions, and the dosage is changeable according to the different time and method of administration as well as the disease itself.

The chromate L-threonate can be used as some clinical drugs to reinforce and cooperate with the physiological function of insulin. For this purpose, chromate L-threonate can be made any preparation, such as tablet, capsule, solution, suspension, emulsion, gelatum, ointment, lyophilized powder, pill, liposome and so on.

The chromate L-threonate can be used as food additive in the form of liquid or solid powder for drinks, cheese, bread, flour etc.

The element analogy of the chromate L-threonate shows in the following table:

|   |       |                     | Element Analogy | |
| - | ----- | ------------------- | ---------------- | ---------------- |
| n | Model | Molecular Formula   | Theoretical Value | Experimental Value |
| 1 | A     | $Cr(C_4H_7O_5)_3 \cdot H_2O$ | C30.31, H4.88 | C29.95, H4.93 |
| 2 | B     | $Cr_2(C_4H_6O_5)_3 \cdot 3H_2O$ | C25.71, H4.32 | C25.56, H4.14 |
| 3 | C     | $Cr(C_4H_5O_5) \cdot 2H_2O$ | C21.71, H4.10 | C21.31, H3.93 |

The characteristics of the chromate L-threonate include:
1. active structure of left-handed rotation
2. stability in high thermal condition (temperature of decomposition>300° C.)
3. dissolution in water (no dissolution in alcohol and ether)

Chromic(III) ion and L-threonic acid can form a stable coordination compound. Although the formation of the coordination is changeable in different pH value solution, there is no precipitate of chromic hydroxide even in basic condition (solution of chromic chloride or chromic sulphate forms precipitate just at pH~4).

The following two charts show the curves of titration and distribution of the reaction in which L-threonic acid and chromic ion form a dibasic coordination compound. According to these curves, we believe that the coordination compound derived from L-threonic acid and chromic ion has enough stability. With computer simulation, the models, stable constant and pH range of the coordination compound are deduced. See the following table:

| Model | Stable Constant | pH |
|-------|-----------------|------|
| B | −0.74 ± 0.34 | 3.5–4.0 |
| A | −4.42 ± 0.14 | ~4.5 |
| C | −9.35 ± 0.26 | ~6.0 |

We select L-threonic acid as the ligand for chromic ion, because L-threonic acid can accelerate the absorption of the ion, also, there is no precipitate of chromic hydroxide even in small intestine (pH~7), thus will improve the absorptive ratio of chromium(III). Meanwhile, it is beneficial to bind with proteins that chromium is taken into the body as the form of chromic(III). Moreover, the chromate L-threonate reinforces the function of insulin by two hands: the activation of chromic ion and the cooperation of L-threonic acid.

According to these advantages, the chromate L-threonate can be applied to a high performance supplement of chromium(III) as well as an effective hypoglycemic treatment for those diabetes patients.

Appendix Figures

Appendix figures of this invention are:

FIG. 1: Titration Curve

Figure 2:
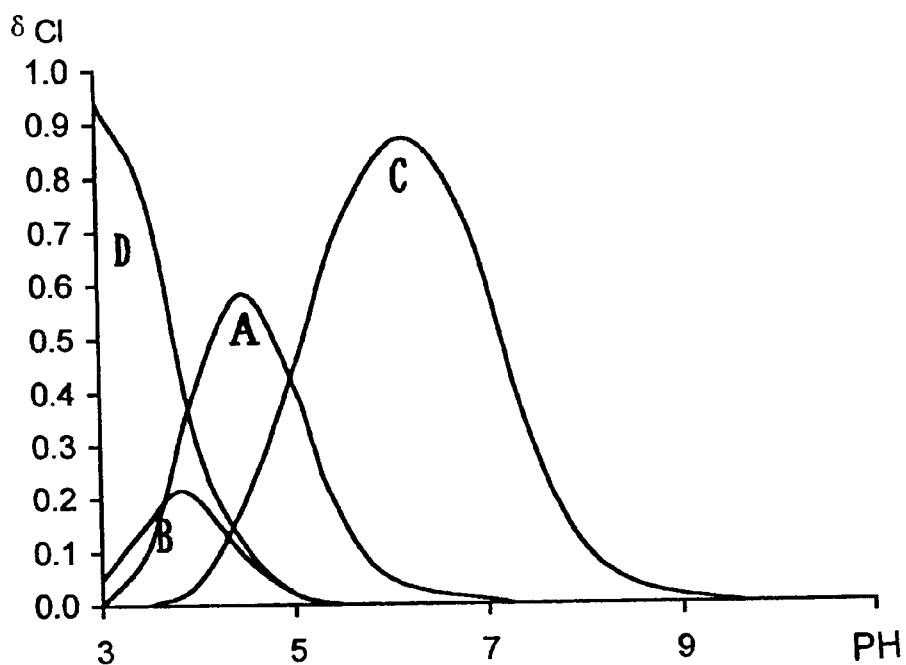

FIG. 2: Distribution Curve

Detail of Synthesis Examples:

The synthesis examples below are explanation to this invention, not limitation.

EXAMPLE 1

The synthesis of the chromate L-threonate: Calcium L-threonate—Chromate L-threonate.

The general reaction formula is:

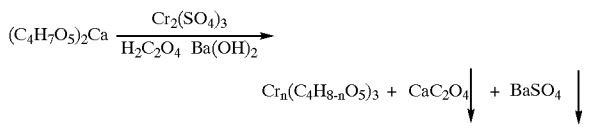

Steps:
1. Dissolve 0.1 mol calcium L-threonate in 600 ml water.
2. Heat the solution to 70° C. and keep 1–3 hours.
3. Add 0.1 mol oxalic crystal—produce white precipitate of calcium oxalate.
4. Cool the mixed solution to room temperature.
5. Filter the mixed solution in decompression and collect the filtrate.
6. Concentrate the filtrate to ⅔ total volume.
7. Dissolve 33 mmol $Cr_2(SO_4)_3 \cdot 6H_2O$ in 100 ml hot water.
8. Add the $Cr_2(SO_4)_3$ solution into the concentrated filtrate of L-threonic acid.
9. Churn the mixed solution completely in 20–50° C. condition.
10. Drop 0.1 mol $Ba(OH)_2$ into the mixed solution with a constant pressure funnel. (control the drop rate at 5 ml/h–15 ml/h)—produce precipitate $BaSO_4$ completely.
11. Filter rapidly the mixed solution in decompression after $Ba(OH)_2$ dropping.
12. Concentrate the filtrate to ⅔ total volume in decompression.

Separate the concentrated filtrate to three same parts, A, B and C, continue the synthesis as follows:

Solution A:

Drop methanol in solution A slowly with churning until the end of precipitating.

Drop another 100 ml methanol.

Filter the mixed solution.

Wash the precipitate three times with anhydrous methanol.

Wash the precipitate twice with anhydrous ether.

Desiccate the precipitate an hour in vacuum dryer.

Product ratio: 31%

Solution B

Adjust pH value of solution B to 3 with L-threonic acid.

Follow the steps as solution A.

Product ratio: 30%

Solution C

Adjust pH value of solution C to 7 with KOH.

Follow the steps as solution A.

Product ratio: 32%

EXAMPLE 2

The synthesis of the chromate L-threonate: Calcium L-threonate—Chromate L-threonate.

The general reaction formula is:

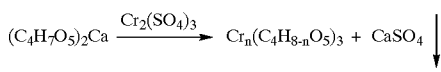

Steps:
1. Dissolve 0.1 mol calcium L-threonate in 600 ml water.
2. Heat the solution to 70° C. and keep 1–3 hours.
3. Dissolve 33 mmol $Cr_2(SO_4)_3 \cdot 6H_2O$ in 100 ml hot water.
4. Add the $Cr_2(SO_4)_3$ into the solution of calcium L-threonate.
5. Churn the mixed solution 4–7 hours.
6. Cool the mixed solution slowly to room temperature.
7. Filter the mixed solution.
8. Concentrate the filtrate to ⅔ total volume.
9. Filter again.
10. Concentrate the filtrate to 100 ml.
11. Separate the concentrated filtrate to three same parts, A, B and C, then follow the steps as Example 1.

The total product ratio is 88%.

EXAMPLE 3

The synthesis of the chromate L-threonate: L-threonic acid—Chromate L-threonate.

The general reaction formula is:

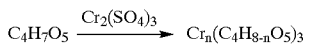

Steps:

I. The synthesis of L-threonic acid:

The reaction formula is:

1. Dissolve 4 g calcium carbonate in 100 ml solution of 0.2 mol/L vitamin C.
2. Drop 10 ml 30% $H_2O_2$ in the mixed solution.
3. Keep the reaction in 30–40° C. condition 1 hour with churning.
4. Add 1.5 g active carbon in and heat the system to 80° C. to destroy ho.

5. Filter the solution while the system is hot.
6. Concentrate the filtrate to ⅓ total volume in decompression at 40° C.
7. Add moderate methanol and keep statically for several hours to precipitate calcium L-threonic acid microcrystal, then filter the mixed solution.
8. Was the microcrystal twice with 80% methanol, then transfer it to a flask.
   (1). Adjust pH value to 5–7 by dropping dilute oxalic acid (sulphuric acid or phosphoric acid). Filter the solution. Keep statically to precipitate the crystal of L-threonic acid. The product ratio is 89%.
   (2). Go to ion-exchange with LR-120 (H$^+$) ion-exchange resin. Collect, concentrate and keep statically the solution to precipitate the crystal of L-threonic acid. The product ratio is 93%.

II. The synthesis of the chromate L-threonate:
1. Dissolve 0.1 mol L-threonic acid in 200 ml water.
2. Dissolve 33 mmol $Cr_2(SO_4)_3 \cdot 6H_2O$ in 100 ml hot water.
3. Add the $Cr_2(SO_4)_3$ in the L-threonic acid solution, mix the solution completely and keep it in 30–40° C. condition.
4. Drop 0.1 mol $Ba(OH)_2$ in the mixed solution with a constant pressure funnel. (control the drop rate at 5 ml/h–15 ml/h)—produce precipitate $BaSO_4$ completely.
5. Filter rapidly the mixed solution in decompression after $Ba(OH)_2$ dropping.
6. Concentrate the filtrate to ⅓ total volume in decompression, and separate it to three same parts, A, B and C, then follow the steps as Example 1.
The product ratio is 86%.

EXAMPLE 4

Tablet of the chromate L-threonate: mix the chromate L-threonate derived from Example 1, 2 or 3 and following material.

| Material | Content |
| --- | --- |
| Chromate L-threonate | 1.5 g |
| Calcium L-threonate | 250 g |
| Mannitol | 180 g |
| Starch | 80 g |
| Essence | moderate |
| Magnesium stearate | moderate |

Make 1000 tablets of the chromate L-threonate by pelletizing, drying and tabletting.

Patients should obey the doctor description when they administrate these tablets.

EXAMPLE 5

Capsule of the chromate L-threonate: mix the chromate L-threonate derived from Example 1, 2 or 3 and following material.

| Material | Content |
| --- | --- |
| Chromate L-threonate | 2.0 g |
| Calcium L-threonate | 300 g |
| Starch | moderate |
| Sodium carboxymethyl-starch | moderate |
| low subsitute hydroxypropylfiber | 10 g |

| Material | Content |
| --- | --- |
| Sodium 12-alkylsulfonate | 8 g |
| No. 0 gastrodissolved capsule | 600 g |

Mix the material above well and make 1000 capsules of the chromate L-threonate.

EXAMPLE 6

Injection of the chromate L-threonate: mix the chromate L-threonate derived from Example 1, 2 or 3 and following material.

| Material | Content |
| --- | --- |
| Chromate L-threonate | 1.0 g |
| Calcium L-threonate | 100 g |
| NaCl | 6.00 g |
| KCl | 0.30 g |
| $CaCl_2 \cdot 2H_2O$ | 0.20 g |
| Water pro injection | moderate |

After dissolving, adjust pH value to be acceptable for human body, add water pro injection to 1000 ml.

Industry Application

We select L-threonic acid as the ligand for chromic ion, because L-threonic acid can accelerate the absorption of the ion, also, there is no precipitate of chromic hydroxide even in small intestine (pH~7), thus will improve the absorptive ratio of chromium(III). Meanwhile, it is beneficial to bind with proteins that chromium is taken into the body as the form of chromic(III). Moreover, the chromate L-threonate reinforces the function of insulin by two hands: the activation of chromic ion and the cooperation of L-threonic acid.

According to these advantages, the chromate L-threonate can be applied to a high performance supplement of chromium(III) as well as an effective hypoglycemic treatment for those diabetes patients.

The chromate L-threonate can be applied to some clinical drugs to reinforce and cooperate with the physiological function of insulin. For this purpose, the chromate L-threonate can be made any form of preparation, such as tablet, capsule, solution, suspension, emulsion, gelatum, ointment, lyophilized powder, pill, liposome and so on.

The chromate L-threonate can be applied to food additive in the form of liquid or solid powder for drinks, cheese, bread, flour etc.

We claim:
1. A chromate L-threonate compound of the following formula:

$$Cr_n(C_4H_{8-n}O_5)_3$$

wherein n represents 1, 2, or 3.

2. A method for producing the chromate L-threonate compound of claim 1, comprising the steps of:
   using calcium L-threonate as starting material to obtain a solution of the chromate L-threonate compound; and
   adjusting the pH of the solution to obtain different coordinate forms of the chromate L-threonate compound in the following formula:

$$(Cr_n(C_4H_{8-n}O_5)_3$$

in which n is 1, 2, or 3.

3. The method according to claim 2, further comprising the steps of:
 (1) reacting the calcium L-threonate with Ba(OH)$_2$ to obtain barium L-threonate; and
 (2) reacting the barium L-threonate with chromate sulphate to obtain the solution of the chromate L-threonate.

4. The method according to claim 2, further comprising the step of:
 reacting the calcium L-threonate with chromate sulphate to obtain the solution of the chromate L-threonate directly.

* * * * *